(12) United States Patent
Maehira

(10) Patent No.: US 7,919,620 B2
(45) Date of Patent: Apr. 5, 2011

(54) AGENT FOR SUPPRESSING BLOOD PRESSURE ELEVATION

(75) Inventor: Fusako Maehira, Okinawa (JP)

(73) Assignee: Coral Biotech Kabushiki Kaisha, Naha-shi (JP)

( * ) Notice: Subject to any disclaimer, the term of this patent is extended or adjusted under 35 U.S.C. 154(b) by 388 days.

(21) Appl. No.: 11/574,817

(22) PCT Filed: Jun. 1, 2005

(86) PCT No.: PCT/JP2005/010037
§ 371 (c)(1),
(2), (4) Date: Mar. 7, 2007

(87) PCT Pub. No.: WO2006/129353
PCT Pub. Date: Dec. 7, 2006

(65) Prior Publication Data
US 2008/0076734 A1    Mar. 27, 2008

(51) Int. Cl.
*A61K 35/02* (2006.01)
*A61K 33/00* (2006.01)
*A61K 33/12* (2006.01)
*A23L 1/304* (2006.01)
*A61P 9/12* (2006.01)

(52) U.S. Cl. .......................................... 546/63; 426/649

(58) Field of Classification Search .................. None
See application file for complete search history.

(56) References Cited

FOREIGN PATENT DOCUMENTS

| JP | 10-120578 | 5/1998 |
|----|-----------|--------|
| JP | 2000-295974 | 10/2000 |
| JP | 2001-048528 | 2/2001 |
| JP | 2001-079566 | 3/2001 |
| JP | 2001-190255 | 7/2001 |
| JP | 2001-190256 | 7/2001 |
| JP | 2003-102423 | 4/2003 |
| JP | 2004-161730 | 6/2004 |
| WO | WO 98/34647 | * 8/1998 |

OTHER PUBLICATIONS

Birchall et al. "Acute toxicity of aluminium to fish eliminated in silicon-rich acid waters." Nature 338:6211, 1898. p. 146-148.*
Li et al. "Inflammation may be a bridge connecting hypertension and atherosclerosis." Medical Hypotheses 64 (5), 2005, p. 925-929. Published online Dec. 24, 2004.*
Ogura, Takeshi. Machine translation of JP 10-120578. Original document published May 12, 1998. Supplied by Industrial Property Digital Library. <http://www.ipdl.inpit.go.jp/homepg_e.ipdl>.*
Yoshinari, Shiyouki. Machine translation of JP 2003-102423. Original document published Apr. 8, 2003. Supplied by Industrial Property Digital Library. <http://www.ipdl.inpit.go.jp/homepg_e.ipdl>.*
Aquabiology, vol. 23, No. 4, pp. 342-349, 2001. (with English abstract).

"Intersalt: an international study of electrolyte excretion and blood pressure. Results for 24 hour urinary sodium and potassium excretion", BMJ, vol. 297, pp. 319-328, Jul 30, 1988.
"Magnesium Deficiency and Hypertension: Correlation Between Magnesium-Deficient Diets and Microcirculatory Changes in situ", Science, vol. 223, pp. 1315-1317, Mar. 23, 1984.
Motoyama, Takaaki et al., "Oral Magnesium Supplementation in Patients with Essential Hypertension", Hypertension, vol. 13, No. 3, pp. 227-232, Mar. 1989.
J. Loeper et al., "The Physiological Role of The Silicon and Its Antiatheromatous Action", Silicon and its anti-Atheromatous Action, pp. 281-297, New York, 1978.
Oceanochemistry. M. Nishimura, ed., Sangyourosho Inc., pp. 101-109, Tokyo, 1994.
Aoki, Kyuzo et al., "Decrease in Blood Pressure and Increase in Total Peripheral Vascular Resistance in Supine Resting subjects with Normotension of Essential Hypertension", Jpn. Heart J., vol. 27, pp. 466-475, Jul. 1986.
Altura M. Burton et al., "Magnesium-Calcium Interrelationships in Vascular Smooth Muscle*)**)", Mag.-Bull., vol. 8, pp. 338-350, 1986.
Altura M. Burton et al., "Magnesium ions and contraction of vascular smooth muscles: relationship to some vascular diseases[1, 2]", Federation Proceedings, vol. 40, No. 12, pp. 2672-2679, Oct. 1981.
Perry, Carole C. et al., "Aspects of the bioinorganic chemistry of silicon in conjunction with the biometals calcium, iron and aluminium", Journal of Inorganic Biochemistry, vol. 69, pp. 181-191, 1998.
Adler, Andrew J. et al., "Uptake, distribution, and excretion of [31]silicon in normal rats", The American Physiological Society, pp. E670-E673, 1986.
Austin, James H., "Silicon Levels in Human Tissues", pp. 255-269, New York, 1978.
Popplewell, J.F. et al., "Kinetics of uptake and elimination of silicic acid by a human subject: A novel application of [32]Si and accelerator mass spectrometry", Journal of Inorganic Biochemistry, vol. 69, pp. 177-180, 1998.
Reffitt, David M. et al., "Silicic acid: its gastrointestinal uptake and urinary excretion in man and effects on aluminum excretion", Journal of Inorganic Biochemistry, vol. 76, pp. 141-147, 1999.
Rondeau, Virginie et al., "Relation between Aluminum Concentrations in Drinking Water and Alzheimer's Disease: An 8-year Follow-up Study", American Journal of Epidemiology, vol. 152, No. 1, pp. 59-66, 2000.
W.S. Broecker et al., "Internal Cycling and Throughput", Pathways from River Mouth to Sea Floor, "Tracers in the Sea", esp., Chapter 1, pp. 1-9, 1982.

* cited by examiner

*Primary Examiner* — Joseph K. McKane
*Assistant Examiner* — Alicia L Otton
(74) *Attorney, Agent, or Firm* — Oblon, Spivak, McClelland, Maier & Neustadt, L.L.P.

(57) ABSTRACT

The antihypertensive agent of the present invention contains a soluble silicon compound. The soluble silicon compound is preferably metasilicic acid or a salt thereof. In one embodiment, the antihypertensive agent of the present invention contains deep sea water containing the soluble silicon compound, or a dried product of such deep sea water. It is preferred that in such embodiment, the antihypertensive agent further contains metasilicic acid or a salt thereof. The amount of silicon present in the deep sea water in the form of silicic acid ($SiO_2$—Si) is 25 µM or more. The deep sea water is typically collected at a depth of 300 m or deeper, and preferably at a depth of 600 m or deeper.

16 Claims, 3 Drawing Sheets

AGENT FOR SUPPRESSING BLOOD PRESSURE ELEVATION

TECHNICAL FIELD

The present invention relates to novel antihypertensive agents and functional food products, including health food products and health supplements that make use of the same agents.

BACKGROUND ART

In our aging society where the relative proportion of people 65 years and older in the entire population is on the increase, the number of patients suffering from high blood pressure, atherosclerosis, and other lifestyle-related diseases has been increasing. The number of individuals who have a high risk of developing such diseases has also been increasing. For example, the majority of adults aged 50 or above develops high blood pressure, a risk factor for diabetes, hyperlipidemia, stroke, heart disease, and other lifestyle-related diseases. It has recently been suggested that people of 50 years old or older also have the risk of a condition known as prehypertension.

High blood pressure results from various causes, including an unbalanced diet, insufficient exercise, and other lifestyle-related factors, stress, intake of vasopressor substances and hereditary traits. These causes are often combined. For this reason, sufferers of high blood pressure need to take different drugs depending on the particular cause to maintain their blood pressure within the normal range. However, it is often difficult to identify and prescribe drugs optimal to a given patient. Furthermore, even when optimal drugs can be prescribed, the patient needs to take such drugs over a long course of treatment, in some cases for the rest of his/her life.

Under such circumstances, the importance of diet in the primary prevention of high blood pressure and other lifestyle-related diseases has become widely recognized. This recognition now serves as the driving force behind the emerging market of health food products, nutritional supplements, food products for specified health uses, nutritionally modified food products, and various other health-oriented functional food products.

Of the many health-oriented functional food products intended for the primary prevention of lifestyle-related diseases including high blood pressure, nutritionally modified functional food products in particular have become widely available. Nutritionally modified functional food products are common food products that have functional or nutritional ingredients added to them. Among such food products are a group of health beverages and food products that make use of intermediate sea water collected at a depth of up to about 300 m. These products, however, are put on the market without scientific investigation of their functionality. There are also health beverages and food products that use deep sea water. In these products, the sea water is generally used as merely a source of minerals (Patent Documents Nos. 1, 2, 3, 4, and 5).

It is known well that Na, Ca, Mg, and other elements are present in sea water (Non-Patent Document No. 6). It is also known well that Na (Non-Patent Document No. 7) and Mg (Non-Patent Document No. 8) play significant roles in the regulation of blood pressure.

One study suggests that what makes deep sea water different from surface sea water is that nutrient salts such as nitrogen-containing salts, phosphorus-containing salts, and silicon-containing salts are present at higher concentrations (Non-Patent Document No. 10). However, no studies have been reported which focus on the ability of deep sea water from the standpoint of the suppression of blood pressure elevation.

As far as silicon (Si) is concerned, it has only been mentioned that in human bodies, the element is most abundant in the aorta and decreases as people grow old, and that the decrease is more prominent in sclerosed arteries than in intact arteries (Non-Patent Document No. 11).

[Patent Document No. 1] Japanese Patent Application Laid-Open No. 2000-295974

[Patent Document No. 2] Japanese Patent Application Laid-Open No. 2001-48528

[Patent Document No. 3] Japanese Patent Application Laid-Open No. 2001-79566

[Patent Document No. 4] Japanese Patent Application Laid-Open No. 2001-190255

[Patent Document No. 5] Japanese Patent Application Laid-Open No. 2001-190256

[Non-Patent Document No. 6] Aquabiology 23(4): 343-349, 2001

[Non-Patent Document No. 7] Brit Med J 297: 319-328, 1988

[Non-Patent Document No. 8] Science 223: 1315-1317, 1984

[Non-Patent Document No. 9] Hypertension 13: 227-232, 1989

[Non-Patent Document No. 10] Aquabiology, 23(4): 343-349, 2001

[Non-Patent Document No. 11] Biochemistry of Silicon and Related Problems, G. Bendz and I. Lindquist, eds., Plenum press, New York, 1978, pp. 281-296.

DISCLOSURE OF THE INVENTION

Problems to be Solved by the Invention

The objective of the present invention thus is to provide a novel antihypertensive agent that has little or no adverse effects on the human body, as well as functional food products such as health food products, health supplements, and the like that use such antihypertensive agents.

The inventors suspected that in addition to such elements as Na, Ca, and Mg, some unknown substances might be present in deep sea water that contribute to human health relating to blood pressure, and have invested significant time and energy in finding such substances. As a result, the inventors have found that deep sea water acts to keep blood pressure low, and that certain soluble silicon compounds present in deep sea water are principally responsible for the action of keeping blood pressure low. These findings eventually led to the development of the present invention.

Accordingly, the present invention provides an antihypertensive agent comprising a soluble silicon compound. Some of the preferred examples of the soluble silicon compound are metasilicic acid and salts thereof.

This antihypertensive agent preferably comprises deep sea water containing a soluble silicon compound, or a dried product of such deep sea water. It is preferred that deep sea water containing the soluble silicon compound, or the dried product thereof, be used in conjunction with metasilicic acid or a salt thereof.

The present invention also offers a health food product or a health supplement comprising the antihypertensive agent.

BEST MODE FOR CARRYING OUT THE INVENTION

Figure 1:
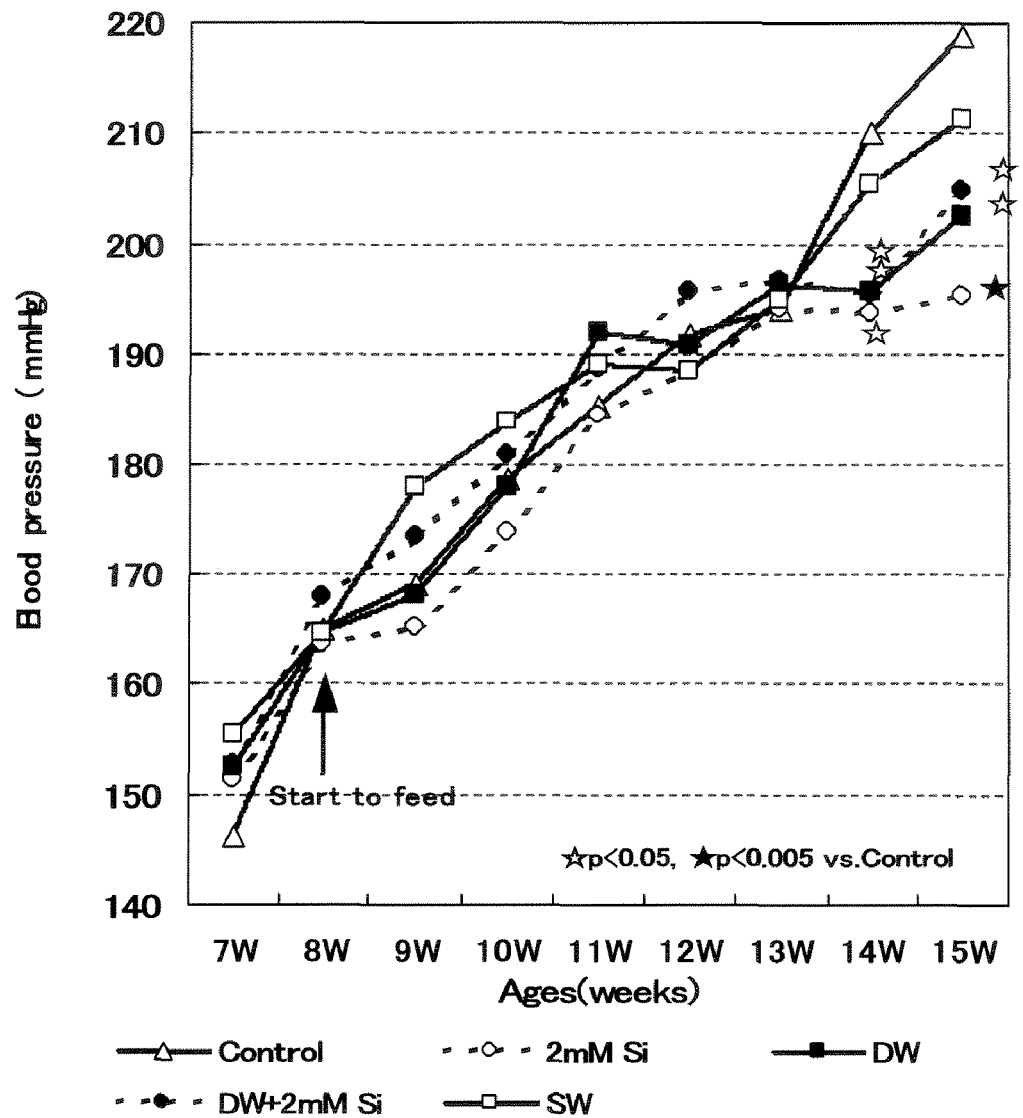
FIG. 1 is a graph showing the change in systolic pressure in rats observed in Example 1, with the horizontal and vertical axes corresponding to the treatment period (age in weeks) and blood pressure (mmHg), respectively.

The soluble silicon compound to serve as the antihypertensive substance of the present invention is preferably metasilicic acid or a salt thereof. Examples of the salt include salts formed with alkali metals such as sodium and potassium.

While the deep sea water to serve as the antihypertensive agent of the present invention is not limited to deep sea water collected from any particular area of the world and may be collected from any part of the world, it preferably contains at least 25 μM, and more preferably at least 40 μM of silicon in the form of silicic acid ($SiO_2$—Si).

The deep sea water for use in the present invention is typically deep sea water collected from a depth of 300 m or more, and preferably deep sea water collected from a depth of 600 m or more.

The dried product of the deep sea water for use in the present invention may be obtained by evaporating water from the above-described deep sea water. The deep sea water may be dried by using any commonly known drying technique, including heat-drying, vacuum-drying, freeze-drying, and spray-drying. Techniques such as that described in Japanese Patent Application Laid-Open No. 2001-48528 may also be used. The technique involves treating the sea water with a reverse-osmotic membrane and concentrating it before drying.

The antihypertensive substance of the present invention may be used in health food products, health supplements, nutritional food products, nutritional supplements, health beverages, and other food products to act to keep the blood pressure of those who consume the products low. These food products are also encompassed by the present invention.

Other food products, food additives, vitamins or/and minerals may be added to the food products of the present invention. Such other food products, food additives, vitamins, or minerals may be any product that is commonly used or expected to be used in pharmaceutical products and food products and does not interfere with the advantages of the present invention.

The food products of the present invention may be provided in the form of a solution, gel, solid, powder, granule, tablet, and capsule and any other suitable form. Any conventional food product (including beverages) containing the antihypertensive substance of the present invention is deemed to be encompassed by the food product of the present invention, regardless of its form.

Examples of such food product include, but are not limited to, beverages, such as soft drinks, nutritional beverages, fruit beverages, and lactic acid beverages (including concentrated stock solutions and conditioned powders of these beverages); frozen sweets, such as ice creams and sherbets; products made from processed cereals, such as soba noodles, udon noodles, bread, rice cakes, rice, pasta, and Chinese dumpling dough; confectionery, such as candies, chocolates, snacks, biscuits, cookies, crackers, jellies, and jams; processed fish and meat products, such as boiled fish cake, puffy fish cake, hams, and sausages; milk products, such as processed milk, cheese, and butter; processed and unprocessed fats and oils, such as margarine, lard, and mayonnaise; seasonings, such as soy sauce, Worcester sauce, fermented soy bean paste, citrus-flavored soy sauce, kelp soup stocks, and soup powders; various side dishes; pickles; various other health and nutritional (supplemental) food products, and the like.

The food products containing the antihypertensive substance of the present invention have significant potential as antihypertensive health (supplemental) food products, such as supplements (referred to as Food for Specified Health Uses, as designated by the Ministry of Health, Labour and Welfare of Japan).

EXAMPLES

The present invention will now be described with reference to examples, which are not intended to limit the scope of the invention in any way.

In the following examples, spontaneously hypertensive rats (SHRs) were used as experimental animals. The antihypertensive effect of deep sea water was examined by comparison with tap water and surface sea water. Specifically, the antihypertensive effect of deep sea water was evaluated from the following three aspects: (1) the antihypertensive effect of the presence of the soluble silicon compound, which is more abundant at greater depths; (2) the antihypertensive effect of the presence of sodium metasilicate nonahydrate ($Na_2SiO_3 \cdot 9H_2O$); and (3) the antihypertensive effect of mixtures of deep sea water and sodium metasilicate. The samples of the sea water used in the examples were collected by the Deep Seawater Laboratory of Okinawa at a point 3 kilometers off the coast of Kumejima island at depths of 612 m (deep sea water) and 15 m (surface sea water).

Example 1

Animal Experiment 1

Comparison of the Antihypertensive Effect of Deep Sea Water, Surface Sea Water, and Soluble Silicon Compound Seven-week-old male SHRs were divided into 5 groups of 6 to 7 animals. Following 1 week of acclimatization, each group was allowed to feed freely on semi-solid feed for 7 to 8 weeks. The feed given was prepared by adding 40 wt % moisture to powdered feed. To ensure that each SHR would develop hypertension, 1 wt % salt was added to the feed. The animals were allowed to freely drink tap water. Over the course of the test period, each animal was weighed and the feed consumption was measured. Blood pressure was taken from the tail vein every four days between 4 PM and 6 PM. After a 12-hour fasting period, the animals were sacrificed. Serum, liver, and kidney were weighed and subjected to analyses.

<Groups and Feed Regimen>

The sea water added was NaCl-removed deep sea water (DW) or NaCl-removed surface sea water (SW) prepared by dialyzation through an electrodialyzer (Asahi Kasei) until the conductivity of monovalent ions was decreased to 10 mS/cm. Table 1 shows the amounts of different types of ions before and after the electrodialysis and the percent removal of each ion species.

The Si concentration in the semi-solid feed containing 40% moisture is defined as the amount of Si contained in 1 kg of the feed. The Si concentration was adjusted by the addition of sodium metasilicate nonahydrate ($Na_2SiO_3 \cdot 9H_2O$).

The groups of rats tested and the corresponding feed regimens are shown in Table 2.

TABLE 1

Results of electrodialysis of sea water using monovalent cationic membrane

| Electro-dialysis | Na (mEq/L) | | Ca (ppm) | | Mg (ppm) | | Si (µM) | |
|---|---|---|---|---|---|---|---|---|
| | DW | SW | DW | SW | DW | SW | DW | SW |
| Before | 458 | 436 | 388 | 388 | 1300 | 1360 | 63.5 | 2.5 |
| After | 16 | 13 | 232 | 232 | 1060 | 1060 | 61.4 | — |
| % removal | 96.5 | 97.0 | 40.2 | 40.2 | 18.5 | 22.1 | 3.3 | — |

TABLE 2

Feeds and corresponding groups

| Group | Feed |
|---|---|
| Control | Normal powdered feed A (CE-2; Clea Japan Inc.) |
| 2 mM Si | Normal powdered feed A + 2 mM Si |
| NaCl-removed deep sea water (DW) | Normal powdered feed A + NaCl-removed deep sea water |
| NaCl-removed deep sea water (DW) + 2 mM Si | Normal powdered feed A + NaCl-removed deep sea water + 2 mM Si |
| NaCl-removed surface sea water (SW) | Normal powdered feed A + NaCl-removed surface sea water |

Results

The results of Example 1 are shown in FIG. 1 and Tables 3 and 4. At age 14 weeks (in week 6 after the start of treatment), a significant difference (by about 15 mmHg) began to be noted in the magnitude of blood pressure elevation between the control group and each of the three groups that were given either 2 mM Si, NaCl-removed deep sea water (DW), or NaCl-removed deep sea water and 2 mM Si ($p<0.05$; FIG. 1 and Table 4). At the end of the test period (15 weeks old), the group given 2 mM Si showed the most significant antihypertensive effect of approximately 23 mmHg ($p<0.005$). The group given NaCl-removed deep sea water (DW) and the group given NaCl-removed deep sea water along with 2 mM Si also showed significant antihypertensive effects of approximately 17 mmHg ($p<0.005$) and 14 mmHg ($p<0.005$), respectively. In comparison, blood pressure suppression was only about 7 mmHg in the group given NaCl-removed surface sea water (SW). No significant differences were observed among the groups in Na intake, water and feed consumption, or body weight at the beginning and the end of the test (Table 3).

TABLE 3

See water-added feed given to SHRs

Groups of 7-week-old male SHRs (7 animals/grp), 8-15 weeks old (56 days)

| Consumption | Control | 2 mM Si | DW | DW + 2 mM Si | SW |
|---|---|---|---|---|---|
| NaCl (mg/day/rat) | 337.7 ± 31.8 [100%] | 344.1 ± 31.0 [101.9%] | 350.0 ± 34.0 [103.6%] | 353.1 ± 27.8 [104.1%] | 353.3 ± 25.2 [105.2%] |
| Water (ml/day/rat) | 22.1 ± 2.3 [100%] | 23.5 ± 5.3 [106.5%] | 25.5 ± 5.3 [115.5%] | 23.7 ± 5.3 [107.5%] | 22.9 ± 3.7 [103.6%] |
| Feed (g/day/rat) | 33.8 ± 3.2 [100%] | 34.5 ± 3.1 [101.9%] | 35.0 ± 3.4 [103.6%] | 35.2 ± 2.8 [104.1%] | 35.6 ± 2.5 [105.2%] |
| Body weight (g) 8 weeks | 188.3 ± 12.1 [100%] | 185.0 ± 12.2 [98.2%] | 185.0 ± 14.3 [96.2%] | 180.2 ± 11.0 [95.7%] | 180.3 ± 15.0 [95.8%] |
| 15 weeks | 300.7 ± 18.1 [100%] | 287.7 ± 14.7 [95.7%] | 290.9 ± 16.5 [96.7%] | 285.2 ± 11.1 [94.8%] | 290.7 ± 17.9 [96.6%] |

TABLE 4

Suppressive effect of sea water-containing feed on the systolic pressure of SHRs

| Age (week) | Systolic pressure of SHRs (mmHg ± SD) | | | | |
|---|---|---|---|---|---|
| | Control | 2 mM Si | DW | DW + 2 mM Si | SW |
| 7 W | 146.2 ± 12.8 | 151.4 ± 9.8 | 152.4 ± 6.5 | 152.6 ± 7.1 | 155.3 ± 6.4 |
| 8 W | 164.9 ± 6.7 | 163.6 ± 7.7 | 164.6 ± 6.4 | 167.9 ± 6.9 | 164.6 ± 8.8 |
| 9 W | 168.9 ± 10.1 | 165.1 ± 9.2 | 168.1 ± 8.7 | 173.2 ± 11.1 | 177.8 ± 11.3 |
| 10 W | 178.6 ± 9.3 | 173.7 ± 12.2 | 177.8 ± 8.6 | 180.7 ± 4.1 | 183.7 ± 8.3 |
| 11 W | 186.3 ± 9.4 | 184.4 ± 11.2 | 191.9 ± 10.3 | 188.7 ± 6.9 | 189.0 ± 11.5 |
| 12 W | 191.7 ± 11.8 | 188.4 ± 10.7 | 190.9 ± 11.7 | 195.7 ± 9.4 | 188.4 ± 14.3 |
| 13 W | 194.1 ± 13.3 | 194.1 ± 10.4 | 196.2 ± 6.9 | 196.6 ± 10.1 | 194.9 ± 11.2 |
| 14 W | 210.1 ± 11.4 | 193.8 ± 11.3[1] | 195.6 ± 7.1[1] | 195.5 ± 10.7[1] | 205.4 ± 9.7 |
| 15 W | 218.8 ± 13 | 195.2 ± 9.8[2] | 202.4 ± 7.4[1] | 204.9 ± 10.3[1] | 211.2 ± 8.8 |

[1]$p < 0.05$,
[2]$p < 0.005$ vs Control

Example 2

Animal Experiment 2

Comparison of the Antihypertensive Effect of Deep Sea Water, Surface Sea Water, and Soluble Silicon Compound Twenty-five 7-week-old male SHRs were divided into 5 groups of 5 animals. Four times as much Si as used in Example 1 was added to the feed given to the rats. Otherwise, the animals were tested under the same conditions as in Example 1. Two types of sea water were added to the powder feed: sea water subjected to NaCl-removing treatment by electrical dialysis and ion-exchanged water. The semi-solid feed containing 1.4 wt % NaCl and 40% moisture was prepared by adding the sea water to powdered feed. The Si concentration was adjusted by the addition of sodium meta-silicate nonahydrate ($Na_2SiO_3 \cdot 9H_2O$). The groups of rats tested and the corresponding feed regimens are shown in Table 5.

TABLE 5

Feeds and corresponding rat groups

| Groups | Feed |
|---|---|
| Control | Normal powdered feed A (CE-2; Clea Japan Inc.) |
| 8 mM Si | Normal powdered feed A + 8 mM Si ($Na_2SiO_3 \cdot 9H_2O$) |
| DW + 8 mM Si | Normal powdered feed A + DW + 8 mM Si |
| SW + 8 mM Si | Normal powdered feed A + SW + 8 mM Si |
| SW + 2 mM Si | Normal powdered feed A + DW + 2 mM Si |

Results

Figure 2:
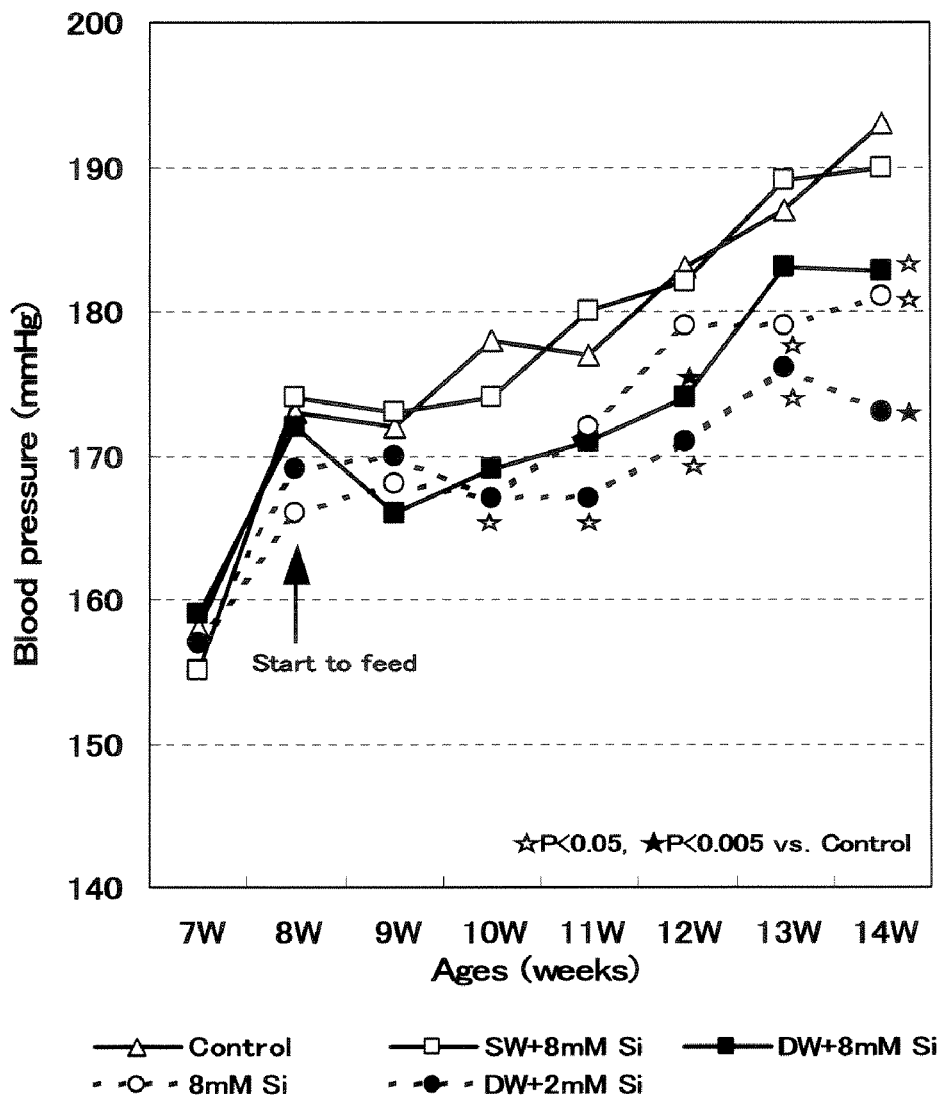
FIG. 2 is a graph showing the change in systolic pressure in rats observed in Example 2, with the horizontal and vertical axes corresponding to the treatment period (age in weeks) and blood pressure (mmHg), respectively.

The results of Example 2 are shown in FIG. 2 and Tables 6 and 7. As shown, the increase in the blood pressure of the Control was suppressed after 10 weeks in each of the three test groups other than the group given surface sea water (SW). At the end of the test period (14 weeks old), a comparable antihypertensive effect of approximately 10 mmHg ($p<0.05$) was observed in each of the groups given deep sea water and 8 mM Si, and the group given 8 mM Si alone. The suppression of the increase in systolic pressure was most significant (20 mmHg difference from the control, $p<0.05$) in the group fed the feed supplemented with deep sea water in which the amount of Si had been decreased from 8 mM to 2 mM. That Si is most effective when added in an optimal range was also confirmed in the aorta smooth muscle cell culture experiment described later in Example 3.

TABLE 6

Sea water-added feed given to SHRs

Groups of 7-week-old male SHRs (5 animals/grp), 7-14 weeks old (49 days)

| Consumption | Control | SW + Si200 | DW + Si200 | DW + Si50 | Si200 |
|---|---|---|---|---|---|
| NaCl (mg/day/rat) | 371.2 ± 58.4 [100%] | 408.6 ± 58.9 [110.1%] | 422.6 ± 73.2 [113.8%] | 426.9 ± 73.6 [115.0%] | 409.4 ± 58.5 [110.3%] |
| Water (ml/day/rat) | 32.1 ± 5.0 [100%] | 38.3 ± 7.8 [119.3%] | 33.4 ± 5.3 [104.0%] | 38.1 ± 7.5 [118.74%] | 34.8 ± 6.4 [108.4%] |
| Feed (g/day/rat) | 28.2 ± 4.4 [100%] | 30.0 ± 4.3 [106.4%] | 30.2 ± 5.2 [107.1%] | 32.0 ± 5.5 [113.4%] | 29.4 ± 4.8 [104.4%] |
| Body weight (g) 8 week | 205.3 ± 12.9 [100%] | 207.1 ± 20.7 [100.9%] | 197.3 ± 18.2 [96.1%] | 200.4 ± 22.7 [97.6%] | 200.3 ± 15.3 [97.6%] |
| 14 week | 296.4 ± 18.2 [100%] | 295.9 ± 21.9 [96.2%] | 290.1 ± 12.9 [97.9%] | 285.2 ± 11.1 [96.2%] | 303.4 ± 22.6 [102.4%] |

TABLE 7

Suppressive effect of sea water-containing feed on the systolic pressure of SHRs

| Age (week) | Systolic pressure of SHRs (mmHg ± SD) | | | | |
|---|---|---|---|---|---|
| | Control | SW + Si200 | DW + Si200 | DW + Si50 | Si200 |
| 7 W | 158 ± 9 | 155 ± 5 | 159 ± 6 | 157 ± 8 | 157 ± 8 |
| 8 W | 173 ± 12 | 174 ± 12 | 172 ± 5 | 169 ± 18 | 166 ± 12 |
| 9 W | 172 ± 7 | 173 ± 8 | 166 ± 5 | 170 ± 11 | 168 ± 4 |
| 10 W | 178 ± 10 | 174 ± 4 | 169 ± 3 | 167 ± 2*[1] | 167 ± 7 |
| 11 W | 177 ± 7 | 180 ± 7 | 171 ± 5 | 167 ± 5*[1] | 172 ± 7 |
| 12 W | 183 ± 2 | 182 ± 2 | 174 ± 2*[2] | 172 ± 9*[1] | 179 ± 4 |
| 13 W | 187 ± 5 | 189 ± 8 | 183 ± 8 | 176 ± 6*[1] | 179 ± 1*[1] |
| 14 W | 193 ± 7 | 190 ± 9 | 183 ± 3*[1] | 173 ± 3*[1] | 181 ± 3*[1] |

*[1] $P < 0.05$,
*[2] $P < 0.005$ vs Control

One possibility is that Na and Mg present in the sea water are responsible for the antihypertensive effect observed in Examples 1 and 2. However, this possibility is rejected by the fact that the concentrations of these elements are substantially the same in surface sea water and deep sea water (Ocean-ochemistry, M. Nishimura, ed., Sangyoutosho Inc., Tokyo, 1994, pp. 101-109., Aquabiology, 23(4): 343-349, 2001). Nevertheless, deep sea water has been demonstrated to exhibit a significantly higher antihypertensive effect as compared to the surface sea water (FIG. 1, Table 4; FIG. 2, Table 7).

As indicated by the results of the figures and tables, deep sea water has proven to exhibit an antihypertensive effect with a significant difference of 5% or higher. This rules out the possibility that the antihypertensive effect observed in Examples 1 and 2 is in fact caused by Na, Mg and other elements that are present at equal concentrations in the surface sea water and deep sea water.

The results of FIG. 1 and Table 4, and FIG. 2 and Table 7 clearly indicate a close correlation of silicon concentration to the antihypertensive effect observed in Examples 1 and 2, a completely new finding. This finding that certain silicon compounds act to keep blood pressure low is truly unprecedented.

It should be appreciated that while the deep sea water used herein was collected from the sea near Kumejima island, Okinawa, deep sea water collected from any part of the world may be used to the same effect.

Example 3

Effect of Soluble Silicon Compound on Mg Uptake by Smooth Muscle Cells of Rat Aorta The mechanism for the antihypertensive effect of the silicon compound as observed in Example 1 was examined in a cell culture experiment using aortic smooth muscle cells (ASMCs) of rats.

It is believed that humans develop primary hypertension as the total peripheral blood vessel resistance increases to push up the blood pressure. The mechanism that causes the increase in total peripheral blood vessel resistance is believed to be that when the intracellular calcium (Ca) level increases, the contraction of the aortic smooth muscles becomes excessive or the relaxation of the muscles becomes incomplete. This causes narrowing of the arterial lumen and thus leads to an increase in the blood pressure (Jpn Heart J 27: 467-474, 1986).

Contrary to the relatively high extracellular Ca level (in the order of 1 mM), the intracellular Ca level must be maintained in the order of 100 nM or less, one ten thousandth of the intracellular level, or lower. This requires complex actions of membrane enzymes.

Magnesium (Mg) is known as a naturally occurring Ca antagonist that inhibits Ca influx from extracellular matrix into cytoplasm (Magnesium-Bulletin 8: 338-350, 1986). Mg present within the cell acts to (i) activate Na—K ATPase (which in turn transports Na out of the cell, resulting in a decreased intracellular Na level), and (ii) activates Mg-sensitive ATPase and adenylate kinase (activation of the enzymes activates Na—K pumps, which facilitate Ca transportation out of the cell, thereby decreasing the intracellular Ca level). As a result, the vascular smooth muscle relaxes to lower the blood pressure (Fed Proc 40: 2672-2679, 1981). One experiment demonstrated that the blood pressure significantly increased in rats fed an Mg-depleted feed, as compared to normally fed rats (Science 223: 1315-1317, 1984). The inhibitory effect of Mg on the contraction of vascular smooth muscles is not its direct action; rather, its inhibitory effect arises usually from the interaction with Ca.

Although each of these two elements is present at an equal concentration in surface sea water and deep sea water, the concentration of the silicon compound in the form of nutrient salts increases at greater depths. Thus, cell culture experiments were conducted to determine if the antihypertensive effect of the soluble silicon compound observed in Example 1 could be based on Mg uptake by the cell and if Mg uptake by the cell could be affected by the amount of Si present. The effect on Ca present in association with Mg was also examined.

(1) Cell Culture Experiment: Effect of Soluble Silicon Compound on Mg Uptake by Rat Aortic Smooth Muscle Cells Rat ASMCs were cultured in Dulbecco's modified Eagle's medium (DMEM) containing 1 mM (physiological blood level) or 4 mM (high conc.) of Mg for 5 days in the presence of either 0 mM, 0.2 mM or 2 mM of Si (in the form of $Na_2SiO_3 \cdot 9H_2O$). Subsequently, the cells were harvested and washed thoroughly to remove the culture medium. The cells were then solubilized with 0.1 N nitric acid and were subjected to atomic absorption spectrometry to determine cellular Mg content. The cell cultures were prepared in triplicate and averages were taken, as shown in Table 8. The results indicate that Mg uptake was relatively high in either of the two Mg levels of culture conditions in the presence of 0.2 mM Si. The results also indicate that Si must be present in a optimal range to facilitate Mg uptake by the cell, especially at the physiological blood level of Mg (1 mM).

TABLE 8

Effect of silicon on Mg uptake by rat ASMCs

| Culture period (days) | Mg content in culture medium (mM) | Si content in culture medium (mM) | Mg content in cells (g/dish) | (%) |
|---|---|---|---|---|
| 5 | 1 | 0 | 34 | 100 |
| | | 0.2 | 60 | 177 |
| | | 2.0 | 46 | 135 |
| | 4 | 0 | 55 | 100 |
| | | 0.2 | 63 | 115 |
| | | 2.0 | 47 | 86 |

Figures in Table 8 are averages of three Petri dishes.

(2) Cell Culture Experiment: Effect of Soluble Silicon Compound on Ca Uptake by Rat Aortic Smooth Muscle Cells $^{45}Ca$ was used to examine the effect of the soluble silicon compound on Ca uptake by ASMCs. The experiment was conducted using the same conditions as in the Mg uptake experiment. Unlike Mg uptake, which was highest in ASMCs cultured in DMEM containing Mg (1 mM) at the blood level and additional 0.2 mM Si, Ca uptake by ASMCs cultured in the presence of 1 mM Ca and 0.2 mM Si was not significantly different (99%) from the Ca uptake by cells cultured in Si-free DMEM medium. The addition of Si had no significant effects on the Ca uptake in ASMCs cultured in the 4 mM Mg culture condition.

TABLE 9

Effect of silicon on Ca uptake by rat ASMCs

| Culture period (days) | Ca content in culture medium (mM) | Si content in culture medium (mM) | Ca content in cells (ng/μg protein) | (%) |
|---|---|---|---|---|
| 5 | 1 | 0 | 0.57 | 100 |
| | | 0.2 | 0.56 | 99 |
| | | 2.0 | 0.62 | 109 |
| | 4 | 0 | 0.63 | 100 |
| | | 0.2 | 0.61 | 96 |
| | | 2.0 | 0.61 | 96 |

Figures in Table 9 are averages of three Petri dishes.

It is considered that substantially all of the membrane-permeable soluble silicon (bioavailable silicon) is present in a living body in the form of non-dissociative monomeric orthosilicic acid $(Si(OH)_4)$ The average blood serum level of the compound is said to be about 20 μM in humans. The non-dissociative form of monomeric orthosilicic acid can be present only in trace amounts in the natural environment: the compound will spontaneously polymerize at room temperature and under atmospheric pressure if present at 2 mM or higher concentrations. During an early stage of polymerization, the compound forms low molecular weight oligomers, which ultimately polymerize into insoluble amorphous silica without fail (Inorg. Biochem., 69, 181-191, 1998). This phenomenon is evidenced by the results of an animal experiment in which the increase in the average blood pressure was suppressed most effectively in groups that were given 2 mM Si alone or deep sea water containing approx. 60 μM Si (Table 1). This was also indicated by the results of an experiment in which the suppression of the increase in blood pressure was more effective in the group that was given deep sea water supplemented with 2 mM Si, a much smaller amount as compared to 8 mM Si.

One proposition is that sodium metasilicate ($Na_2SiO_3$) is converted to metasilicate ($H_2SiO_3$), part of which is then converted, in an equilibrium state, to one chemical form of Si compound that is present in deep sea water and is readily absorbed from the cell membrane. It may be this form of Si compound that has an antihypertensive effect. It is considered that the soluble silicon detected in deep sea water is present in the form of monomeric orthosilicic acid ($Si(OH)_4$). A rational explanation for these observations is that the antihypertensive effect of soluble Si is mediated by acceleration of the Mg uptake by the cells. This implies that sodium metasilicate and deep sea water each have an antihypertensive effect.

Example 4

Animal Experiment 3

Effect of Soluble Silicon Compound on the Increase of Blood Pressure Under Mg-Depleted Conditions In the above-described experiment, we have demonstrated that Mg uptake by ASMCs increases when the cells are cultured in the presence of Si and physiological level of Mg (Table 8) In this experiment, we examine how this phenomenon observed in the cell culture is reflected in the suppression of blood pressure increase in animals.

Figure 3:
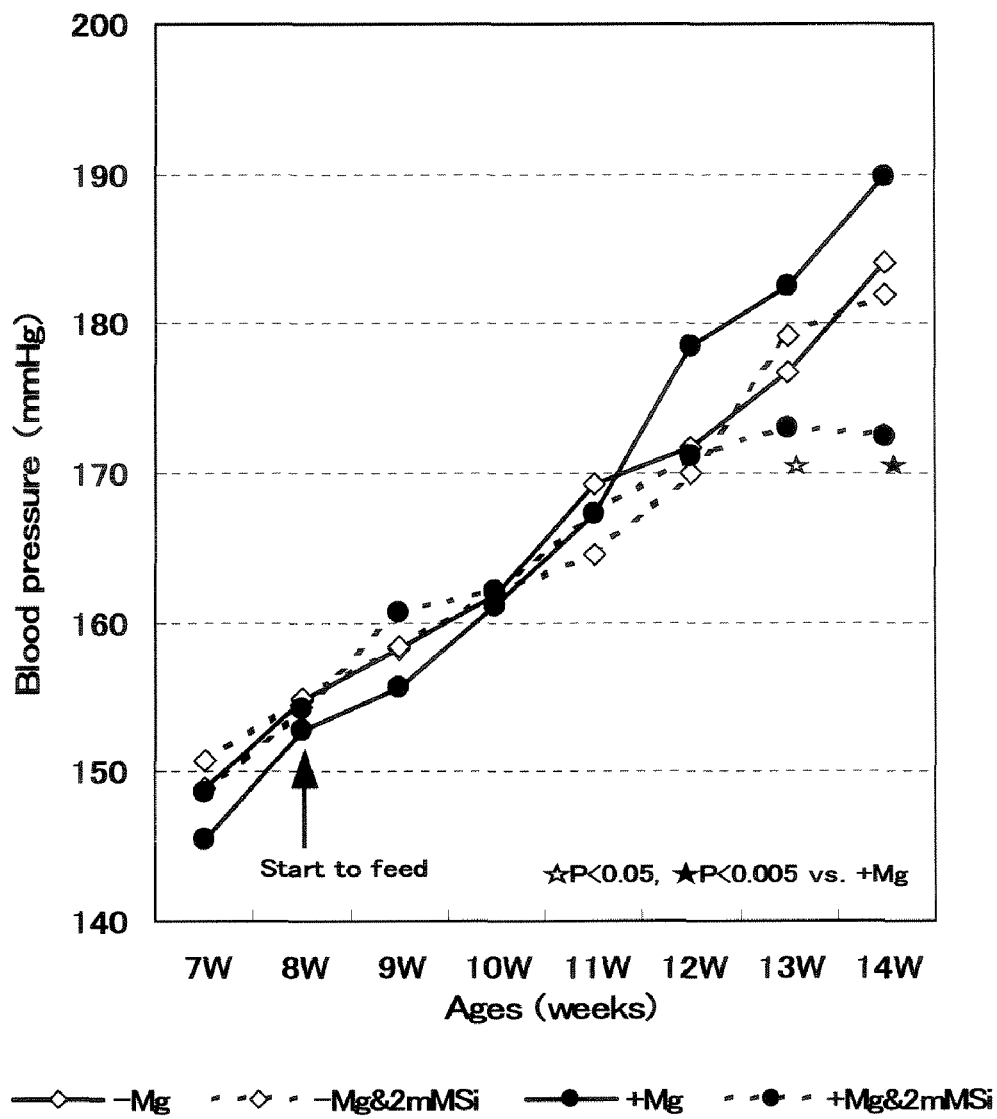
FIG. 3 is a graph showing the change in systolic pressure in rats observed in Example 4, with the horizontal and vertical axes corresponding to the treatment period (age in weeks) and blood pressure (mmHg), respectively.

The addition of Si caused no significant difference in systolic pressure between the groups given the Mg-depleted feed, whereas the increase in systolic pressure was significantly suppressed in the groups given feed containing Mg along with Si after 12 weeks. In these groups, suppression of the blood pressure increase was as much as approx. 20 mmHg (at a significance level of P<0.005) at the end of the test period (14 weeks old) (FIG. 3, Table 11).

The groups fed Mg-depleted feed or Mg-depleted feed with 2 mmol Si added consumed approx. 20% less feed than the two groups given Mg-containing feed. This was reflected in the significant decrease in body weight and Na intake (Table 10). The difference in the body weight increase became particularly significant after age 11 weeks.

TABLE 10

Mg-containing or Mg-free feed given to SHRs

| Consumption | Groups of 7-week-old male SHRs (7 animals/grp) | | | |
|---|---|---|---|---|
| | +Mg | +Mg & 2 mM Si | −Mg | −Mg & 2 mM Si |
| NaCl (mg/day/rat) | 348.8 ± 44.4 [100%] | 381.1 ± 38.5 [92.5%] | 247.7 ± 44.7 [79.9%]*[1] | 278.9 ± 63.7 [81.0%]*[1] |
| Water (ml/day/rat) | 29.1 ± 4.4 [100%] | 30.0 ± 6.2 [103.3%] | 32.2 ± 5.2 [111.1%]*[1] | 29.3 ± 6.6 [100.8%] |
| Feed (g/day/rat) | 29.0 ± 3.8 [100%] | 26.8 ± 3.2 [92.5%] | 23.2 ± 3.8 [79.9%] | 23.5 ± 5.4 [81.0%]*[1] |
| Body weight (g) 8 week | 213.9 ± 6.7 [100%] | 209.5 ± 8.2 [97.9%] | 215.9 ± 5.9 [100.9%] | 209.1 ± 9.3 [97.8%] |
| 14 week | 298.4 ± 11.0 [100%] | 304.4 ± 20.3 [102.0%] | 262.7 ± 10.0 [88.0%]*[2] | 253.0 ± 11.1 [84.8%]*[2] |

*[1]$p < 0.05$,
*[2]$p < 0.005$ vs +Mg

TABLE 11

Suppressive effect of Mg-containing or Mg-free feed on the systolic pressure of SHRs

| Age (week) | Systolic pressure of SHRs (mmHg ± SD) | | | |
|---|---|---|---|---|
| | +Mg | +Mg & 2 mM Si | −Mg | −Mg & 2 mM Si |
| 7 W | 145.5 ± 9.3 | 148.7 ± 7.3 | 148.9 ± 6.2 | 150.8 ± 6.0 |
| 8 W | 152.8 ± 3.9 | 154.2 ± 7.1 | 154.8 ± 5.0 | 154.9 ± 6.3 |
| 9 W | 155.6 ± 5.8 | 160.7 ± 2.9 | 158.2 ± 7.7 | 156.4 ± 3.6 |
| 10 W | 161.1 ± 4.2 | 162.1 ± 6.4 | 161.9 ± 3.8 | 162.0 ± 4.7 |
| 11 W | 167.3 ± 6.6 | 167.3 ± 8.8 | 169.3 ± 5.4 | 164.6 ± 5.2 |
| 12 W | 178.4 ± 5.8 | 171.1 ± 7.8 | 171.8 ± 6.6 | 170.0 ± 6.8 |
| 13 W | 182.4 ± 4.9 (100) | 173.0 ± 8.4 (94.8)*[1] | 176.7 ± 5.1 (96.9)*[1] | 179.1 ± 6.4 (98.2) |
| 14 W | 189.8 ± 5.5 (100) | 172.4 ± 4.1 (90.8)*[2]*[a]*[b] | 184.0 ± 6.1 (96.9) | 181.9 ± 9.8 (95.8) |

*[1]$p < 0.05$,
*[2]$p < 0.005$ vs +Mg,
*[a]$p < 0.001$ vs −Mg
*[b]$p < 0.05$ vs −Mg & 2 mM Si

Concerning the non-toxic nature of the soluble inorganic silicon compound, one study demonstrated that orthosilicic acid $^{31}Si(OH)_4$ (labeled with Si isotope with a half life of $T_{1/2}$=156 min), when delivered into the rat heart, was present mostly in its free form with no proteins bound to it. The study also showed that 77±12% of the delivered amount was excreted in urine within 4 hours with little found in the brain (Am. J. Physiol. 251 (Endocrinol. Metab. 14): E670-E673, 1986.). In another study, 27 mice, 3 rabbits, 1 monkey, and 1 dog were given water (with Si added) containing 0.005% (50 ppm), 0.1% or 2.0% of $Na_2SiO_3.9H_2O$ for 4 months, and no changes were observed in the appearance of the brain, heart, kidney, liver, or spleen, nor were there any changes observed when the tissue samples were stained and analyzed by microscopy. No changes were observed in the Si content of these organs after the animals were given water containing 0.1% (1000 ppm) Si over a 17-month period (Biochemistry of Silicon and Related Problems, G. Bendz and I. Lindquist, eds., Plenum Press, New York, 1978, pp. 255-268.).

According to a recent report, when human subjects were given orthosilicic acid $^{32}Si(OH)_4$ ($T_{1/2}$=approx. 150 years), 36% was absorbed and detected in the blood. 90% of the absorbed compound was excreted into urine with $T_{1/2}=2.7$ hours. The remaining 10% was excreted with $T_{1/2}=11.3$ hours. The absorbed Si was completely removed after 48 hours (J. Inorg. Biochem., 69: 177-180, 1998). In one study, 8 healthy volunteers were given an aqueous solution of ortho-silicic acid (27-55 ppm). 50.3% (range: 21.9-74.7%, n=8) of the ingested orthosilicic acid was absorbed. Renal clearance of Si was 82-96 ml/min and showed a high correlation with creatinine clearance, indicating high renal filtration (J. Inorg. Biochem., 76: 141-147, 1999).

These studies suggest that soluble inorganic silicon compounds, when ingested, are readily removed from the body and cause no harm. In a recent epidemiological study, in which a cohort of 3777 elderly people aged 65 or older were monitored for 8 years to determine the correlation of the Al level in drinking water (a potential risk factor for onset of dialysis dementia and Alzheimer's disease in patients on renal dialysis) with the onset of dementia, it was suggested that a high level (11.25 mg/L or more) of silica in drinking water can protect the elderly people from the high risk of Al toxicity (Am. J. Epidemiol. 152(1): 59-66, 2000).

INDUSTRIAL APPLICABILITY

The following antihypertensive agents, provided in accordance with the present invention, can be directly ingested to keep blood pressure low and thereby achieve an antihypertensive effect: antihypertensive agents comprising deep sea water containing a soluble silicon compound that increases at greater depths; antihypertensive agents containing sodium metasilicate nonahydrate ($Na_2SiO_3 \cdot 9H_2O$) as the soluble silicon compound; and antihypertensive agents containing deep sea water along with sodium metasilicate. The same advantages may be obtained by ingesting functional beverages and food products that have the above antihypertensive agents added to them.

The invention claimed is:

1. A composition comprising:
   (a) deep sea water, which has been collected from a depth of at least 300 m; optionally after removal of sodium chloride; and
   metasilicic acid or a salt thereof; or
   (b) deep sea water, which has been collected from a depth of at least 300 m, from which the water has been removed, optionally after removal of sodium chloride; and
   metasilicic acid or a salt thereof.

2. The composition of claim 1, wherein the deep sea water is collected from a depth of at least 600 m.

3. The composition of claim 1, wherein the deep sea water has been treated to remove sodium chloride.

4. The composition of claim 1, wherein the deep sea water has been treated to remove sodium chloride until the conductivity of monovalent ions in said composition is decreased to 10 mS/cm or until the monovalent sodium ion concentration ranges between 13 and 16 mEq/L.

5. The composition of claim 1, part (a) which contains at least 25 μM of silicon in the form of silicic acid.

6. The composition of claim 1, part (a) which contains at least 40 μM of silicon in the form of silicic acid.

7. The composition of claim 1 that comprises a salt of metasilicic acid which is a sodium or potassium salt.

8. The composition of claim 1 in dehydrated form.

9. A food comprising the composition of claim 1.

10. A supplement comprising the composition of claim 1.

11. A method for treating hypertension comprising administering to a subject in need thereof an effective amount of the composition of claim 1.

12. A composition comprising:
    deep sea water containing a soluble silicon compound or a dried product thereof, wherein the deep sea water has been collected from a depth of at least 300 m, and
    metasilicic acid or a salt thereof,
    wherein the deep sea water has been treated to remove sodium chloride.

13. The composition of claim 12, wherein the deep sea water has been treated to remove sodium chloride until the conductivity of monovalent ions in said composition is decreased to 10 mS/cm or until the monovalent sodium ion concentration ranges between 13 and 16 mEq/L.

14. A method for treating hypertension comprising administering to a subject in need thereof an effective amount of the composition of claim 12.

15. An antihypertension agent comprising the composition of claim 1.

16. An antihypertension agent comprising the composition of claim 12.

* * * * *